July 10, 1956 M. L. WHISLER Plant Pat. 1,496
ROSE PLANT
Filed Aug. 23, 1955
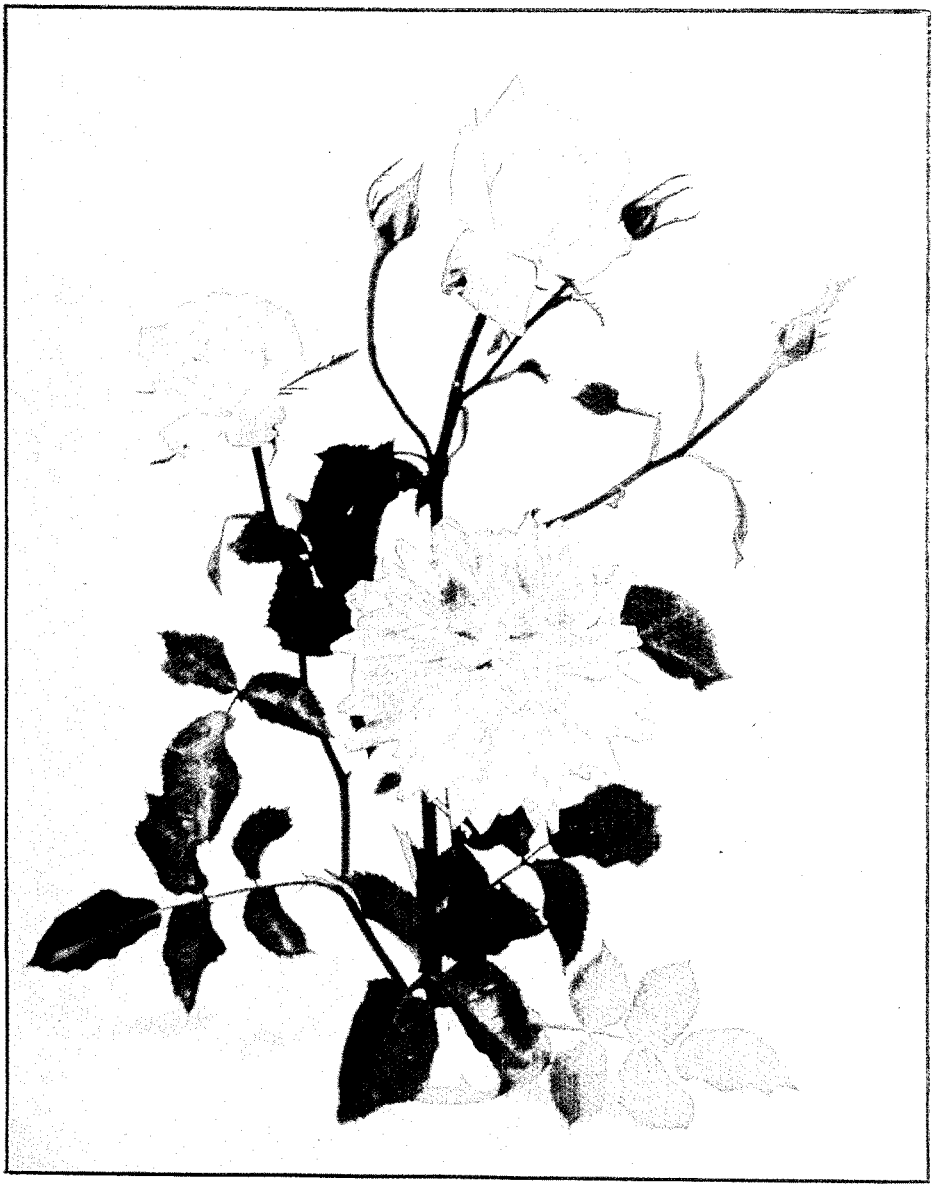
Inventor.
M. L. Whisler
By: Robb & Robb
Attorneys

United States Patent Office

Plant Pat. 1,496
Patented July 10, 1956

1,496

ROSE PLANT

Milton L. Whisler, Granada Hills, Calif., assignor to Germain's, Inc., Van Nuys, Calif., a corporation of California

Application August 23, 1955, Serial No. 530,221

1 Claim. (Cl. 47—61)

The present invention relates to a new and distinct variety of rose plant of the hybrid polyantha class, which was originated by me by crossing an unnamed and unpatented seedling of "Herrenhausen" (unpatented) × "Golden Rapture" (unpatented) with the variety "Easter Parade" (Plant Patent No. 1,200).

As the result of this breeding, I have produced a new rose variety which is a substantial improvement over "Easter Parade" and which is particularly distinguished from that parent, as well as from all other varieties of its class, by its tall, upright and vigorous growth, and the extreme and distinctive color change of the petals of its flowers, said color change ranging from a deep Yellow-Orange to a deep Rose Red color as the flower matures.

Asexual reproduction of my new variety by budding, as performed by me at Saugus, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Type: Half-hardy; tall; bush; outdoor; seedling; for garden decoration.
Class: Hybrid polyantha.
Breeding: Seedling.
*Seed parent.*—An unnamed seedling of "Herrenhausen" × "Golden Rapture."
*Pollen parent.*—"Easter Parade."
Propagation: Holds its distinguishing characteristics through succeeding propagations by budding.

FLOWER

Locality where grown and observed: Saugus, California.
Flowers borne: Sometimes singly, and sometimes several to stem in irregular, pyramidal cluster; on stems of medium length and normal strength.
Quantity of bloom: Free, outdoors.
Continuity: Intermittent.
Fragrance: Very slight. Nature—spicy.
Bud:
*Peduncle.*—Short; medium caliper; erect; smooth; with few Red hairs. Color—Reddish Bronze.
*Before calyx breaks.*—Size—small. Form—short; ovoid; with foliaceous appendages on the surface of the bud; with stout, much-cut foliaceous parts extending beyond the tip of the bud equal to more than its length. Color—Light Green.
*As calyx breaks.*—Color—Cardinal Red, Plate 822.
*As first petal opens.*—Size—small. Form—short; pointed. Color: Outside—Spanish Orange, Plate 010, washed with Cardinal Red, Plate 822/1 only where sunlight strikes petal. Inside—Spanish Orange, Plate 010/1.
*Opening.*—Opens up well.

Bloom:
*Size (when fully open).*—Small; from 2 inches to 3 inches.
*Petalage.*—Very double; from 65 to 70 petals; arranged irregularly.
*Form.*—Cupped at first, but becoming open; petals being at first loosely rolled outward, but later becoming tightly rolled outward at maturity.
Petals:
*Texture.*—Thick; leathery; with inside velvety and outside satiny.
*Shape.*—Lanceolate.

This description of a newly opened flower was made from a rose grown outdoors in the month of June, at Saugus, California:

*Color.*—Outer petal: Outside surface—Cherry, Plate 722/3; inside surface—Straw Yellow, Plate 604/1, shaded Rose Opal, Plate 022/1, where sunlight strikes petal. Intermediate petal: Outside surface—Straw Yellow, Plate 604/2; inside surface—Straw Yellow, Plate 604/1, washed with Coral Pink, Plate 0619/2 where sunlight strikes petal. Inner petal: Outside surface—Coral Pink, Plate 0619; inside surface—Coral Pink, Plate 0619.

This description was made from a rose that was open for 3 days outdoors in the month of June, at Saugus, California:

*Color.*—Outer petal: Outside surface—Straw Yellow, Plate 604/2, shaded with Cherry, Plate 722/3; inside surface—Straw Yellow, Plate 604/2, shaded with Cherry, Plate 722/3. Inner petal: Outside surface—Naples Yellow, Plate 403/3, shaded with Rose Madder, Plate 23/1; inside surface—Rose Red, Plate 724.
*General color effect.*—Newly opened flower—Chinese Coral, Plate 614/1. 3-days open—Rose Red, Plate 724.
*Behavior.*—Persist; fading Brown; not affected by weather.
*Flower longevity.*—On bush in garden—5 days in June. Cut roses grown outdoors and kept at livingroom temperature—2 days in June.

REPRODUCTIVE ORGANS

Stamens: Very few; arranged irregularly; tucked in calyx.
Filaments: Medium length; most with anthers. Color—Straw Yellow.
Anthers: Medium size; open at various times. Color—Straw Yellow.
Pollen: Very sparse. Color—Yellow.
Pistils: Medium number.
Styles: Uneven; some short and some medium length; medium caliper; loosely bunched.
Stigma: Color—White and Yellow.
Ovaries: All enclosed in calyx.
Hips: Globular; with inconspicuous neck; smooth; thin walls. Color—Green-Gray.
Sepals: Falling soon; long; straight.
Seeds: Few and small.

PLANT

Foliage:
*Leaves.*—Compound of 3 to 5 leaflets; normal abundance; medium size; moderately heavy and leathery.

*Leaflets.*—Shape—Oval, with apex obtuse. Base—obtuse. Margin—irregularly serrate.

*Color.*—Mature: Upper surface—Dark Green; under surface—moderately Gray-Green. Young: Upper surface—Light Bronze Red; under surface—moderately Green Bronze.

*Rachis (the supporting stem of the compound leaf).*—Upper side—grooved; hairy. Under side—sparsely prickly.

*Stipules.*—Moderately short; wide; with short points turning out at an angle of 45°.

*Disease resistance.*—Good resistance to mildew as compared with other varieties grown under comparable cultural conditions at Saugus, California.

Growth:

*Habit.*—Bushy; upright; much-branched.

*Growth.*—Vigorous.

*Canes.*—Medium caliper.

*Main stems.*—Color—Dull Green Red. Thorns—few; long; hooked downward; with long, narrow base. Prickles—none. Hairs—none.

*Branches.*—Color—Dull Bronze Red. Thorns—few; long; straight; with long, narrow base. Prickles—none. Hairs—none.

*New Shoots.*—Color—Dull Bronze Red. Thorns—very few; long; straight; with long, narrow base. Prickles—none. Hairs—none.

I claim:

A new and distinct variety of rose plant of the hybrid polyantha class, substantially as herein shown and described, characterized particularly as to novelty by its tall, upright, vigorous growth, and the extreme color change of it flower petals ranging from deep Yellow-Orange to deep Rose Red as the flowers mature.

No references cited.